(12) United States Patent
Friel (10) Patent No.: US 11,701,481 B2
(45) Date of Patent: Jul. 18, 2023

(54) SPACER

(71) Applicant: AER BEATHA LIMITED, London (GB)

(72) Inventor: Michael Friel, London (GB)

(73) Assignee: AER BEATHA LIMITED, London (GB)

( * ) Notice: Subject to any disclaimer, the term of this patent is extended or adjusted under 35 U.S.C. 154(b) by 445 days.

(21) Appl. No.: 16/626,966

(22) PCT Filed: Jul. 3, 2018

(86) PCT No.: PCT/EP2018/067965
§ 371 (c)(1),
(2) Date: Dec. 27, 2019

(87) PCT Pub. No.: WO2019/007968
PCT Pub. Date: Jan. 10, 2019

(65) Prior Publication Data
US 2020/0282158 A1    Sep. 10, 2020

(30) Foreign Application Priority Data

Jul. 3, 2017 (GB) ..................................... 1710621

(51) Int. Cl.
*A61M 15/00* (2006.01)

(52) U.S. Cl.
CPC ...... *A61M 15/0088* (2014.02); *A61M 15/009* (2013.01); *A61M 2205/0238* (2013.01); *A61M 2207/00* (2013.01)

(58) Field of Classification Search
CPC .......... A61M 15/0086; A61M 15/0088; A61M 15/009; A61M 2205/02; A61M 2205/0233; A61M 2205/0238; A61M 2207/00

USPC ......................................................... 162/139
See application file for complete search history.

(56) References Cited

U.S. PATENT DOCUMENTS

| | | | |
|---|---|---|---|
| 6,202,643 B1 | 3/2001 | Sladek | |
| 6,550,473 B1* | 4/2003 | Sladek | A61M 15/0086 128/200.22 |
| 8,801,899 B1* | 8/2014 | Reed | D21H 17/72 162/123 |
| 2002/0129814 A1 | 9/2002 | Sladek | |
| 2007/0283954 A1 | 12/2007 | Dhuper et al. | |
| 2010/0163045 A1* | 7/2010 | Powell | A61M 15/0088 128/203.29 |
| 2013/0025594 A1* | 1/2013 | Wachtel | A61M 15/0088 128/203.28 |

(Continued)

FOREIGN PATENT DOCUMENTS

| | | |
|---|---|---|
| EP | 2 783 590 A1 | 10/2014 |
| WO | 01/05458 A1 | 1/2001 |

(Continued)

OTHER PUBLICATIONS

"Iggesund Product Catalogue 2015-2016", 2015 (Year: 2015).*

(Continued)

*Primary Examiner* — Colin W Stuart
*Assistant Examiner* — Douglas Y Sul
(74) *Attorney, Agent, or Firm* — Oliff PLC (57) ABSTRACT

An inhalation spacer movable between a collapsed configuration and an expanded configuration. The spacer is made from paperboard having a bending stiffness of at least 2.5 mNm.

20 Claims, 9 Drawing Sheets

(56) References Cited

U.S. PATENT DOCUMENTS

| | | | |
|---|---|---|---|
| 2013/0276781 A1* | 10/2013 | Steelman | A61M 15/0013 |
| | | | 128/203.12 |
| 2016/0194527 A1* | 7/2016 | Bloembergen | B32B 29/005 |
| | | | 536/56 |
| 2016/0208440 A1* | 7/2016 | Byrd, Jr. | B65D 85/1045 |
| 2017/0181469 A1 | 6/2017 | Poget et al. | |
| 2019/0151578 A1* | 5/2019 | Dennis | A61M 15/0088 |

FOREIGN PATENT DOCUMENTS

| | | |
|---|---|---|
| WO | 2008/021451 A2 | 2/2008 |
| WO | 2008/124666 A2 | 10/2008 |
| WO | 2009/018397 A1 | 2/2009 |

OTHER PUBLICATIONS

"Thayer LiteAire Valved Holding Chamber Instructions for Use", ref 1303, 2015 (Year: 2015).*

Dec. 19, 2017 Search Report issued in Great Britain Patent Application No. GB1710621.2.

Oct. 1, 2018 Search Report issued in International Patent Application No. PCT/EP2018/067965.

Oct. 1, 2018 Written Opinion issued in International Patent Application No. PCT/EP2018/067965.

\* cited by examiner

SPACER

FIELD OF INVENTION

The present invention relates to an inhalation spacer. The present invention relates to an inhalation spacer which is of particular, but not exclusive, use with pressurised metered dose inhaler (pMDI) devices.

BACKGROUND

It is known to provide inhalation spacers for use with medical inhaler devices, in particular pressurised metered dose inhaler (pMDI) devices. Spacers provide a large-volume air flow-path between the outlet of an inhaler device and the mouth of a patient.

By providing such an air flow-path between an inhaler device and the mouth of the patient, delivery of aerosolized medication into the lungs of a user is improved.

Spacers slow the speed at which the aerosolized medication enters the mouth of a patient, preventing the medication from striking the back of the mouth. A low-velocity plume of aerosolized medication is therefore allowed to develop in the air flow-path. Low velocity plumes of aerosolized medication are known to be most effective for delivery deep into the lungs, maximising the delivered dose of medication.

Without wishing to be bound by theory, it is considered that large particles of aerosolized medication (typically >5 μm in diameter) are non-respirable. Particles of this size either evaporate into smaller particles when the low-velocity plume forms in the air flow-path, or coalesce and precipitate.

The aerosolized plume of medication can remain in the large-volume air flow path of the spacer for a number of seconds before being inhaled, thereby eliminating the need for the user to accurately coordinate the ejection of aerosolized medication from a drug reservoir with inhalation. This coordination can be particularly challenging for children and the elderly. Advantageously, a user can also inhale more slowly when using a spacer.

Inhalation spacers are conventionally made from plastic. However, plastic spacers can carry static charge. Build-up of static charge in such spacers is problematic, because aerosolized medications are attracted to the static charge, causing them to adhere to the inner walls of the spacer by electrostatic attraction. The dose of medication delivered to the lungs is therefore reduced. In order to ameliorate the problem of static attraction, plastic spacers are often primed with several dosages of an aerosolised medication. This process is wasteful.

Traditional plastic spacers are generally large, and as such are only used in the home or in medical practices. They are rarely used 'on the move', and so compliance is poor.

In more recent years, various collapsible paper spacers have been developed. The LiteAire® spacer from Thayer, and the Livingstone™ spacer, are two such examples of collapsible paper spacers.

These paper spacers are collapsible for storage, and have a small-volume flow-path (typically up to 200 mL). They are therefore more portable than conventional plastic spacers. However, the small volume of these known paper spacers does not support formation of an effective low-velocity plume.

A significant drawback with known collapsible paper spacers is that they have low durability. In particular, they are made of paperboard materials which have a low folding endurance (i.e. are susceptible to cracking from repeated folding). They are therefore sold as disposable spacers, for use over short periods of time (typically up to a week). The known paper spacers are perforated in order to provide fold-lines. These perforations create weak points in the product, thereby reducing durability.

The present invention aims to provide a spacer which reduces, ameliorates, or even eliminates one or more of the problems of low medical efficacy, low portability, and low durability.

SUMMARY OF INVENTION

In a first aspect, the present invention provides an inhalation spacer movable between a collapsed configuration (e.g. for storage) and an expanded configuration (e.g. for use with an inhaler device), wherein the spacer is made from paperboard having a bending stiffness of at least 2.5 mNm.

The inventor has found that paperboard having a bending stiffness of 2.5 mNm) can be used to form a spacer which can be moved between its collapsed and expanded configurations repeatedly (e.g. hundreds, or even thousands, of times) without becoming damaged, e.g. without forming cracks along lines along which it is folded.

Bending stiffness is a measure of the stiffness of paperboard when bent. It may be measured using standardised test ISO 5628:2012. Bending stiffness is commonly measured using a Messmer-Büchler stiffness tester by measuring the force required to bend a single layer of paperboard by 5°.

In some embodiments, the bending stiffness of the paperboard may be at least 3 mNm or at least 3.5 mNm, e.g. at least 3.7 mNm.

The bending stiffness of the paperboard may be at most 85 mNm. For example, the bending stiffness of the paperboard may be at most 80 mNm, e.g. at most 77.9 mNm.

The paperboard may have a bending stiffness of between 5 and 40 mNm.

The fibres of the paperboard may have a generally laminar orientation. The direction parallel to the laminar orientation of the fibres may be referred to as the 'machine direction'. The direction perpendicular to the laminar orientation of the fibres may be referred to as the 'cross direction'.

The paperboard may have a first bending stiffness in the machine direction and a second bending stiffness in the cross direction.

The first bending stiffness may be higher than the second bending stiffness.

The first bending stiffness may be at least 5 mNm. In some embodiments, the first bending stiffness is at least 8 mNm, e.g. at least 8.2 mNm.

The first bending stiffness may be at most 80 mNm, e.g. at most 77.9 mNm. In some embodiments, the bending stiffness in the machine direction may be between 35 mNm and 40 mNm, e.g. around 38.5 mNm.

The second bending stiffness may be at least 2.5 mNm, e.g. at least 3 mNm, or even at least 3.7 mNm. The second bending stiffness may be at most 40 mNm, e.g. at most 34 mNm. In some embodiments, the bending stiffness in the cross direction may be between 15 mNm and 20 mNm, e.g. around 16 mNm.

The paperboard may have a bending moment of at least 1 mNm, e.g. at least 1.4 mNm. Preferably, bending moment is determined by measuring the bending moment required to bend paperboard by an angle of e.g. 15°. Measurement of bending moment is done using a Taber stiffness tester (ISO 2493). The bending moment of the paperboard may be at least 2 mNm, e.g. at least 2.2 mNm. The bending moment may be at most 45 mNm, e.g. less than 40 mNm. In some embodiments, the bending moment of the paperboard may be between 1 and 20 mNm.

The paperboard may have a first bending moment in the machine direction and a second bending moment in the cross direction.

The first bending moment may be higher than the second bending moment.

The first bending moment may be at least 3 mNm. The first bending moment may be at least 4.4 mNm, e.g. at least around 4.6 mNm.

The first bending moment may be at most 45 mNm. The first bending moment may be at most 40 mNm. In some embodiments, the first bending moment may be between 17 and 22 mNm, e.g. around 20 mNm such as around 19.6 mNm.

The second bending moment may be at least 1 mNm. The second bending moment may be at least 1.4 mNm, e.g. at least 2 mNm, or even at least 2.2 mNm. The second bending moment may be at most 20 mNm, e.g. at most 19 mNm. In some embodiments, the second bending moment may be between 5 mNm and 10 mNm, e.g. around 9 mNm such as around 8.7 mNm.

The paperboard may have a tensile strength of at least 9 kN/m, e.g. at least 9.5 kN/m. The paperboard may have a tensile strength of at most 35 kN/m, e.g. at most 31.5 kN/m. Tensile strength may be determined according to the standardised test ISO 1924-2:2008, which provides a measure of the elastic elongation of the paperboard under tensile force.

The paperboard may have a first tensile strength in the machine direction and a second tensile strength in the cross direction.

The first tensile strength may be higher than the second tensile strength.

The paperboard may have a first tensile strength of at least 15 kN/m. The paperboard may have a first tensile strength of at least 17 kN/m, e.g. at least 18.5 kN/m. The paperboard may have a first tensile strength of at most 35 kN/m, e.g. at most 32 kN/m. In some embodiments, the paperboard may have a first tensile strength of between 20 kN/m and 30 kN/m, e.g. around 25 or 25.5 kN/m.

The paperboard may have a second tensile strength of at least 7 kN/m. The paperboard may have a second tensile strength of at least 9 kN/m, e.g. around 10 kN/m. The paperboard may have a second tensile strength of at most 15 kN/m, e.g. at most 14.5 kN/m. In some embodiments, the paperboard may have a second tensile strength of between 10 kN/m and 15 kN/m, e.g. around 12.5 kN/m.

The paperboard may have a first tearing resistance in the machine direction and a second tearing resistance in the cross direction.

The first and/or second tearing resistance may be at least 1800 mN, e.g. at least 2000 mN, or at least 2300 mN. The first and/or second tearing resistance may be at most 6500 mN, e.g. at most 6400 mN. In some embodiments, the paperboard may have a first tearing resistance of around 4300 mN. In some embodiments, the paperboard may have a second tearing resistance of around 4600 mN. Tearing resistance may be measured according to the standardised test ISO1974:2012, by measuring the tensile force required to tear a single layer of the paperboard.

References herein to paperboard mean a fibrous, paper-based material with an area density of at least 150 g/m². The unit of g/m² may alternatively be referred to as 'grammage'.

The paperboard may have an area density of at least 180 g/m², e.g. at least 200 g/m². The paperboard may have an area density of at most 995 g/m², e.g. at most 680 g/m², e.g. at most 500 g/m², such as at most 400 g/m². In some embodiments, the paperboard may have an area density of around 300 g/m².

The paperboard may comprise a single layer or may comprise multiple layers affixed (e.g. glued) together such that the paperboard has a laminated structure. The individual layers in the laminate structure may have the same or different properties e.g. the same or different area density. In the case of the multi-layer laminate paperboard, the defined bending stiffness, bending moment, tensile strength, tearing resistance and area density is for the laminated structure rather than for each individual layer within the laminated structure.

The paperboard may have a thickness of at least 200 µm, such as at least 230 µm. The paperboard may have a thickness of at most 600 µm, e.g. at most 510 µm. In some embodiments, the paperboard may have a thickness of around 395 µm. The fibres of the paperboard may have a fibre length of between 0.8 and 4.5 mm. In some embodiments, the fibres of the paperboard have fibre length between 0.9 and 3.5 mm.

In some embodiments, the paperboard comprises fibres having a length between 0.9 and 1.2 mm and/or fibres having a length between 2 and 3 mm and/or fibres having a length between 3.1 and 3.5 mm.

The paperboard may comprise fibres derived from a plurality of different wood sources. The fibres derived from each wood source may have a different length from one another.

For example, the paperboard may comprise fibres having a length between 0.9 and 1.2 mm derived from a first wood source and/or fibres having a length between 2.0 and 3.0 mm derived from a second wood source and/or fibres having a length between 3.1 and 3.5 mm derived from a third wood source.

The paperboard may comprise fibres derived from Spruce and/or Pine and/or Birch. In some embodiments, the paperboard comprises Spruce and Pine fibres.

For example, the paperboard may comprise fibres having a length between 0.0.9 and 1.2 mm derived from Birch and/or fibres having a length between 2 and 3 mm derived from Pine and/or fibres having a length between 3.1 and 3.5 mm derived from Spruce.

The fibres may have a width of greater than 15 microns e.g. equal to or greater than 19, 20 or 22 microns. The fibres may have a maximum width of 50 microns e.g. a maximum width of 35 microns.

For example, in some embodiments, the paperboard comprises fibres having a length between 0.9 and 1.2 mm and a width between 20 and 35 microns and/or fibres having a length between 2 and 3 mm and a width between 22 and 50 microns and/or fibres having a length between 3.1 and 3.5 mm and a width between 19 and 50 microns.

The fibres may be primary fibres (otherwise known as virgin fibres). Accordingly, the paperboard may be virgin paperboard. In some embodiments, the paperboard does not contain any recycled fibres.

The fibres may be chemically pulped fibres. In particular, the paperboard may be formed from a chemical pulping process, e.g. from the chemical pulping of wood chips. In some embodiments, the chemical pulping process used is sulphate chemical pulping.

The fibres of the paperboard may be bleached. In particular, the pulp obtained by the chemical pulping process may be bleached. Accordingly, the paperboard may be solid bleached board (SBB) paperboard.

Pulping and bleaching processes may collectively remove 80-90% of lignin from the raw material.

Accordingly, the paperboard may comprise up to 10% by mass, e.g. up to 5% by mass, of lignin. The paperboard may comprise at least 70% by mass of cellulosic fibres, and a balance of other plant-originating and/or non-plant-originating materials.

The cellulosic fibres may comprise cellulose fibres, and hemicellulose fibres. In this case, the paperboard may comprise at least 45% by mass of cellulose, e.g. at least 50% by mass of cellulose. The paperboard may comprise at least 25% by mass of hemicellulose, e.g. at least 30% by mass of hemicellulose.

At least one (and optionally both) surfaces of the paperboard may comprise at least one coating layer.

The coating layer may be a water-resistant (e.g. waterproof) layer.

The coating may be a pigmented (e.g. white) coating to provide a surface suitable for printing.

For example, the coating layer (e.g. the water-resistant coating layer) may comprise a clay or mineral material such as china clay and/or calcium carbonate. It may further comprise a binder material e.g. starch, soy protein or an acrylate binder.

The coating may be an anti-static coating.

The balance of non-plant-originating materials mentioned above may include the material of the coating layer.

The spacer has a collapsed and expanded configuration, meaning that the spacer is significantly more portable than known plastic spacers. Furthermore, by providing a spacer made of paperboard (which does not readily carry electrostatic charge), the present invention significantly reduces the problem of aerosolized medication adhering to the spacer (e.g. to the inner surfaces of the spacer).

The spacer may have a substantially flat profile in the collapsed configuration. The total external volume of the spacer in the collapsed configuration may be less than 10% of the total external volume of the spacer in the expanded configuration. The total external volume of the spacer in the collapsed configuration may be less than 5% of the total external volume of the spacer in the expanded configuration.

In the expanded configuration, the spacer may have an internal cavity, the internal cavity providing an air flow-path between an inlet aperture and an outlet aperture. The internal cavity may have a volume of 500 mL or more in the expanded configuration. The internal cavity may have a volume of 1000 mL or less e.g. 750 mL or less in the expanded configuration.

The inventor has found that an internal cavity volume of between 500 mL and 1000 mL provides a good balance between medical efficacy and portability.

The volume of the internal cavity in the collapsed configuration may be less than 10% of its volume in the expanded configuration. The volume of the internal cavity in the collapsed configuration may be less than 5% of its volume in the expanded configuration.

The volume of the internal cavity in the collapsed configuration may be less than 50 mL. The volume of the internal cavity is substantially zero in the collapsed configuration. In other words, there may be effectively no internal cavity in the collapsed configuration.

The spacer may have a length, measured from the inlet aperture to the outlet aperture, of at least 5 cm. The length may be at least 7.5 cm e.g. at least 10 cm.

The inlet aperture may be configured for engagement with a mouthpiece of a medical inhaler device. In particular, the inlet aperture may comprise a recess portion for intimate, e.g. substantially air-tight, engagement with the mouthpiece of an inhaler device.

The outlet aperture may be configured for engagement with the mouth of a patient/user. In particular, the size of the outlet aperture may be selected so that a user can place his/her mouth over the outlet aperture to inhale.

In some embodiments, the inlet and outlet apertures are located at opposing axial ends of the spacer from each other.

The internal surface of the spacer, e.g. the internal surface of the internal cavity, may comprise the coating layer. In some embodiments, the entire internal surface of the internal cavity comprises the coating layer (as described above).

The outer surface of the spacer may comprise the coating layer. In some embodiments, the entire outer surface of the spacer comprises the coating layer (as described above).

The spacer may comprise upper and lower portions defining the air flow-path, and first and second axial end portions located at respective axial ends of the air flow-path (e.g. defining the axial ends of the internal cavity). The inlet aperture may be formed in the first axial end portion, and the outlet aperture may be formed in the second axial end portion.

All of the upper and lower and two axial end portions may be formed from a single piece (blank) of folded paperboard.

The upper and lower portions may have a substantially rectangular or square profile and are joined to one another along their opposing lateral edges. One join between the lateral edges of the upper and lower portions may be a fold and one may be an adhesively-connected join.

In the expanded configuration each of the upper and lower portions is convex, the convexity of the upper and lower portions defining the internal cavity.

In the expanded configuration, the convexity of the upper and lower portions may be maintained by concave axial end portions, the concave axial end portions having a profile which is substantially a mandorla-shape. For each of the axial end portions, one of the opposing mandorla edges will be connected/joined to the axial edge of the upper portion and the other to the axial edge of the lower portion.

The joins between the axial end portions and the upper/lower portions may be folded joins or may be adhesively-connected joins.

In the collapsed configuration, the upper and lower portions may be planar and may overlay one another. In the collapsed configuration, the axial end portions may be laterally folded i.e. with a fold (either inwards or outwards) along an edge/join between the axial end portions and the upper/lower portions, and/or a fold between the apices of the mandorla shape.

In this way, the spacer has a substantially flat profile in the collapsed configuration.

In some embodiments, the air flow path has a constant internal cross-section from the inlet aperture to the outlet aperture. Similarly, the external cross-sectional profile of the spacer, from the first axial end portion to the second axial end portion, may be constant. The cross-sectional profile of the air flow path/spacer may match the profile of the axial end portions e.g. it may be mandorla-shaped.

The air flow-path between the inlet aperture and the outlet aperture may be uninterrupted. In particular, the spacer may comprise a single, continuous internal cavity extending from the inlet aperture to the outlet aperture. In these embodiments, there is no valve or obstruction provided in the air flow-path.

The spacer may be expandable by forcing the first and second axial end portions towards each other (e.g. into their concave profile), thereby forcing the upper and lower portions away from each other (e.g. into their convex profile) to form the internal cavity.

The spacer may be collapsible by forcing the upper and lower portions towards each other (e.g. into a planar, overlaying arrangement), thereby folding the axial end portions to eliminate the internal cavity.

In some embodiments, the spacer is packaged (e.g. for sale) and distributed in the collapsed configuration, and transported by a user in the collapsed configuration.

Creases may be provided in the paperboard, to provide folding points (e.g. fold lines, or hinges) about which the spacer is movable between the collapsed and expanded configurations. In particular, the creases may provide fold-lines, e.g. along the joins between the upper, lower and axial end portions.

In some embodiments, the creases are provided at the joins between the upper portion, lower portion, first axial end portion, and second axial end portion of the spacer. In particular, the creases may be located at the edges of the spacer in the expanded configuration.

Each crease may have the appearance of a corrugation, or furrow, in the surface of the paperboard. In some embodiments, the creases do not include perforations.

The creases may each have width of between 0.8-1.5 mm, such as between 0.9-1.4 mm. The creases may each have a depth of between 0.4-0.8 mm, such as between 0.5-0.7 mm.

In some embodiments, the creases may each have a width of around 1 mm (e.g. around 1.2 mm), and a depth of around 0.5 mm (e.g. around 0.6 mm).

Alternatively, fold-lines may be provided by score-lines in a surface of the paperboard.

In some embodiments, the paper spacer is formed from a single paperboard blank. In other words, the paper spacer may be formed from a single piece of paperboard, joined to itself at opposing edges to form the spacer of the first aspect.

DESCRIPTION OF DRAWINGS

Embodiments of the invention are set out below in detail, with reference to the accompanying drawings, in which.

DETAILED DESCRIPTION

The following detailed description of embodiments of the present invention is made by way of example. On reading this disclosure, modifications of the embodiments that fall within the scope of the invention will be apparent.

Manufacture of the paperboard used to form the inhalation spacer according to an embodiment of the present invention will first be described.

Figure 1A:
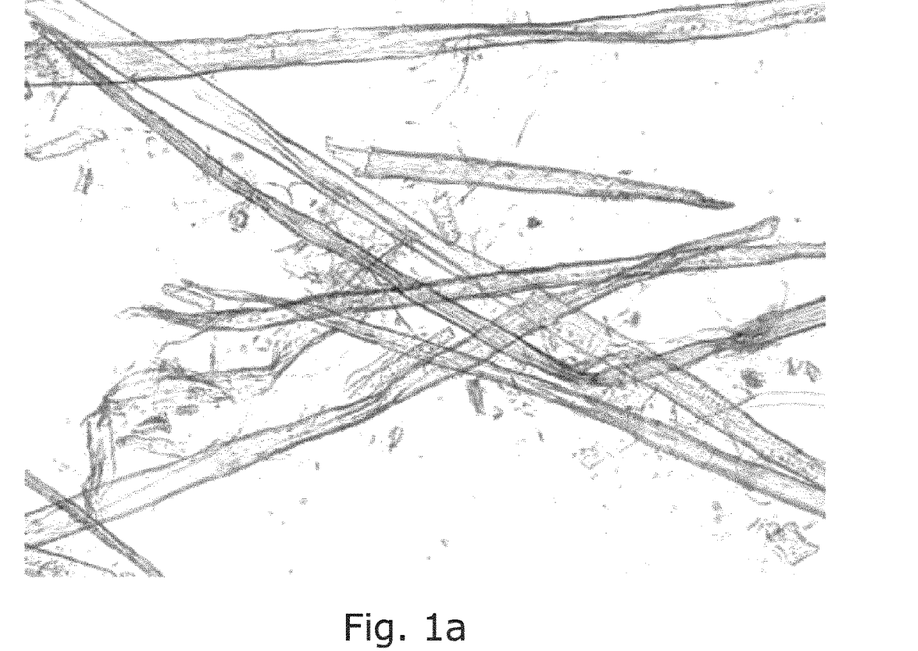
FIG. 1a shows a microscope image of Spruce fibres.
Figure 1B:
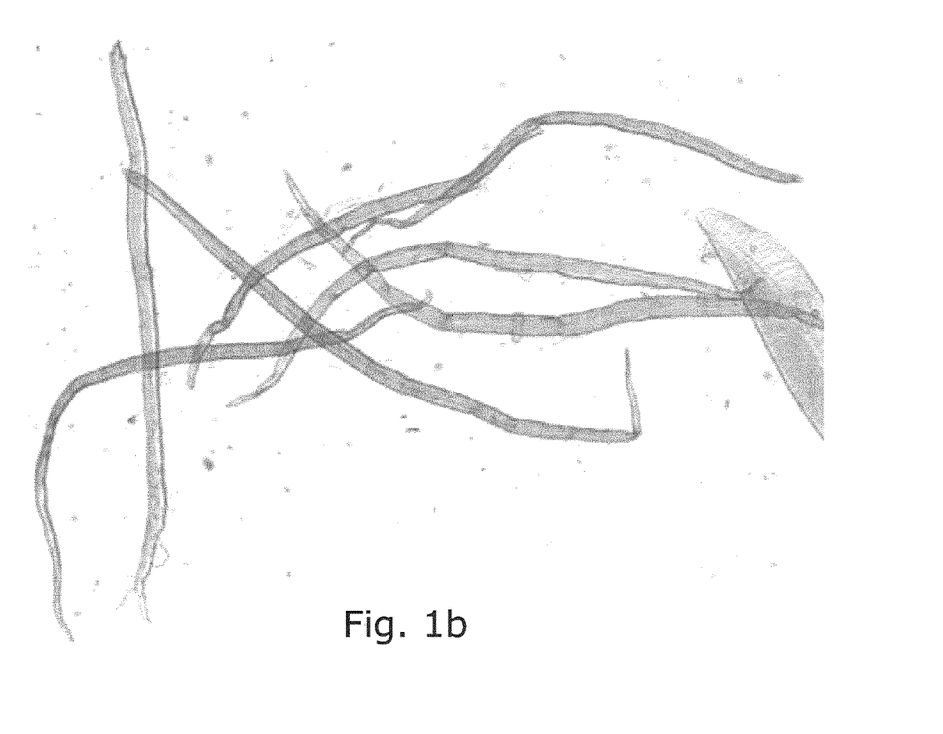
FIG. 1b shows a microscope image of Birch fibres
Figure 1C:
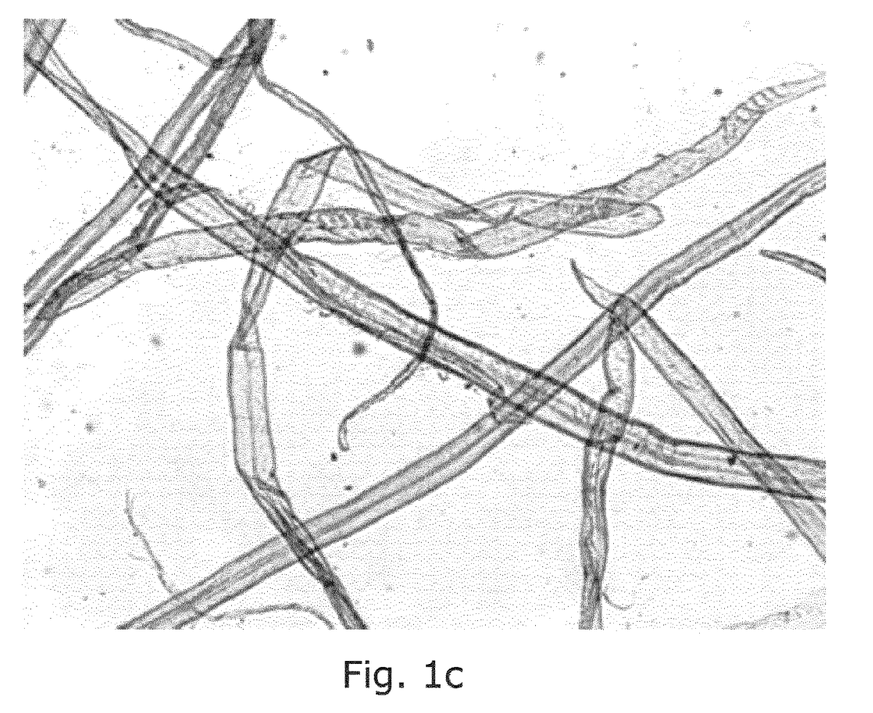
FIG. 1c shows a microscope image of Pine fibres.
Figure 1D:
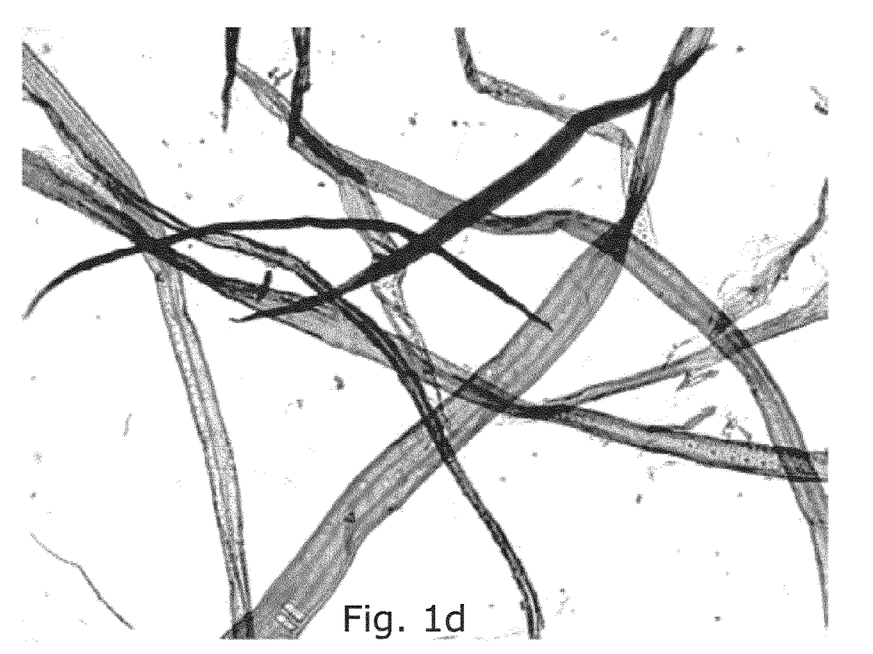
FIG. 1d shows a microscope image of a blend of Spruce, Pine and Birch fibres.

The paperboard comprises a mixture of Spruce, Pine and Birch fibres. These species of tree grow well in cold climates, and have a far longer average fibre length than trees that grow in warmer climates. FIGS. 1a, 1b and 1c show microscope images of Spruce, Birch and Pine fibres (respectively). The length of the fibres can be clearly seen. The fibres are extracted from Pine, Birch and Spruce sourced from Scandinavia and northern Europe, where average year-round temperatures are low. Low temperatures further contribute to the fibres being long. FIG. 1d shows a microscope image of a blend of Pine, Spruce and Birch fibres.

TABLE 1

Fibre length, width and shape

| Species | Fibre length (mm) | Fibre width (µm) | Fibre shape |
|---|---|---|---|
| Spruce | 3.1-3.5 | 19-50 | Ribbon-like, flat |
| Pine | 2-3 | 22-50 | Ribbon-like, flat |
| Birch | 0.9-1.2 | 20-35 | Cylindrical, pointed ends |

The raw wood product is first de-barked, and formed into wood chips.

The fibres are extracted from the raw wood material by a combination of sulphate chemical pulping, and bleaching. These processes remove 80-90% of lignin (which would otherwise affect the foldability and folding endurance of the paperboard), leaving a white (colourless) pulp consisting mainly of cellulose and hemicellulose fibres.

Waste products, e.g. bark and lignin, can be used in energy generation, in order to avoid wasting the raw material.

Once extracted, the pulp is suspended in water, to a concentration of at least 1% (1 part pulp fibres, to 99 parts water). The pulp suspension is then allowed to settle onto a wire mesh, to form multiple layers of fibres. Once the desired thickness of fibres has formed on the mesh, they are dried, and vacuum-pressed. The paperboard material is then pressed and dried. This process encourages the fibres bind to each other in the paperboard, forming an interlocking fibrous network. The binding is helped by the presence of hemicellulose fibres. The fibres give the paperboard excellent folding endurance, withstanding up to 2,700 folds before becoming permanently damaged, e.g. before forming cracks along fold-lines. In other words, the fibres improve foldability and folding endurance.

The resulting product is solid bleached board (SBB) paperboard, which comprises multiple laminar layers of high-purity cellulose and hemicellulose fibres.

This SBB paperboard is pure, hygienic, safe for medical applications, and compliant with European Union and American food contact regulations. It conforms to the good manufacturing practices (GMP) for food, drug products and pharmaceuticals. It is also approved for use with foods by the food standards agency (FSA).

The SBB paperboard does not contain recycled or mechanically pulped fibres. The process used to recycle paper-based products causes a reduction in fibre length. By using virgin, or primary, fibres for the paperboard (rather than recycled fibres), maximum fibre length (and hence maximum folding endurance) is achieved. Also, by using chemical pulping rather than mechanical pulping, reduction in fibre length is avoided.

Finally, the outer surfaces of the SBB paperboard are coated with a ceramic coating layer, typically china clay and/or calcium carbonate. The coating layer enables high-quality graphics to be printed onto the SBB paperboard, by preventing ink bleed. Advantageously, the coating layer is water-resistant so that the spacer can be easily cleaned, e.g. wiped down, thereby improving hygiene of the product such that it is suitable for repeated use in medical applications.

Figure 2:
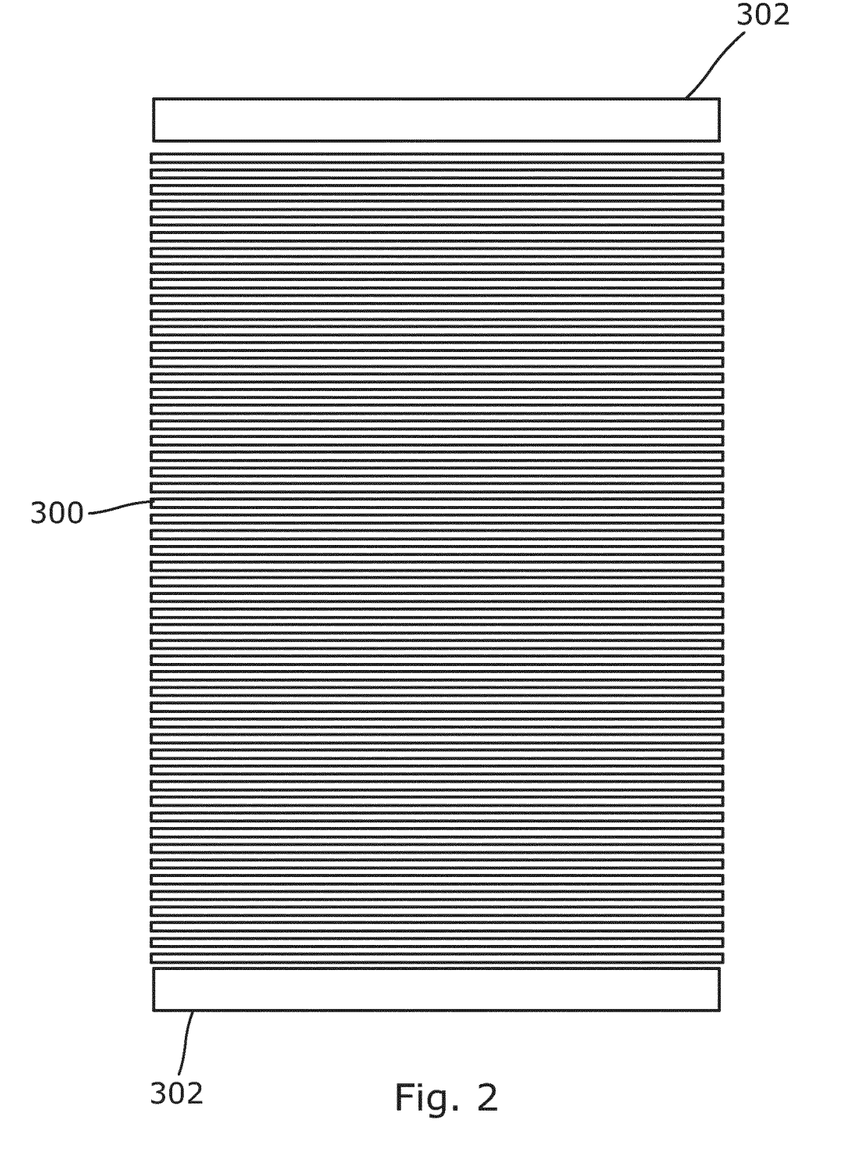
FIG. 2 is a schematic illustration of the composition of SBB paperboard.

FIG. 2 shows a schematic illustration of the SBB paperboard, with a central laminated bleached chemical pulp layer 300 sandwiched between coating layers 302. The inventor has found that paperboard with an area density of between 180 g/m² to 400 g/m² e.g. around 300 g/m² gives a suitable foldability and folding endurance.

Properties of the paperboard (e.g. SBB paperboard) used in embodiments of the present invention will now be described.

The fibres in paperboard materials tend to have a generally laminar orientation, in the plane of the paperboard. Reference herein to the machine direction means in a direction parallel to the laminar orientation of the fibres. Reference herein to cross direction in means in a direction perpendicular to the laminar orientation of the fibres, i.e. perpendicular to the machine direction.

Specific mechanical properties for a particular SBB paperboard ranging from 180 g/m² to 380 g/m² are given in Table 2, below. The inventor has found that paperboard with an area density of 300 g/m² has a particularly desirable combination of foldability and folding endurance for use in the present invention.

In particular, foldability is defined according to equation 1, below. As can be seen, foldability depends on mending moment, in addition to bending stiffness. As bending stiffness increases, so does foldability. Foldability is a dimensionless unit.

Foldability=bending stiffness/bending moment

Table 3 below shows foldability values of paperboard suitable for use in the spacer of the present invention.

TABLE 3

Foldability of SBB paperboard between 180 g/m² and 380 g/m².

| Grammage (g/m²) | Foldability | |
|---|---|---|
| | Machine direction | Cross direction |
| 180 | 1.77 | 1.79 |
| 200 | 1.78 | 1.68 |
| 220 | 1.75 | 1.74 |
| 240 | 1.76 | 1.88 |
| 260 | 1.76 | 1.87 |
| 280 | 1.97 | 1.89 |
| 300 | 1.96 | 1.84 |
| 330 | 1.92 | 1.89 |
| 350 | 1.97 | 1.88 |
| 380 | 1.97 | 1.86 |

A method by which the spacer of the present application may be produced (e.g. using the paperboard disclosed above) will now be described.

Figure 3:
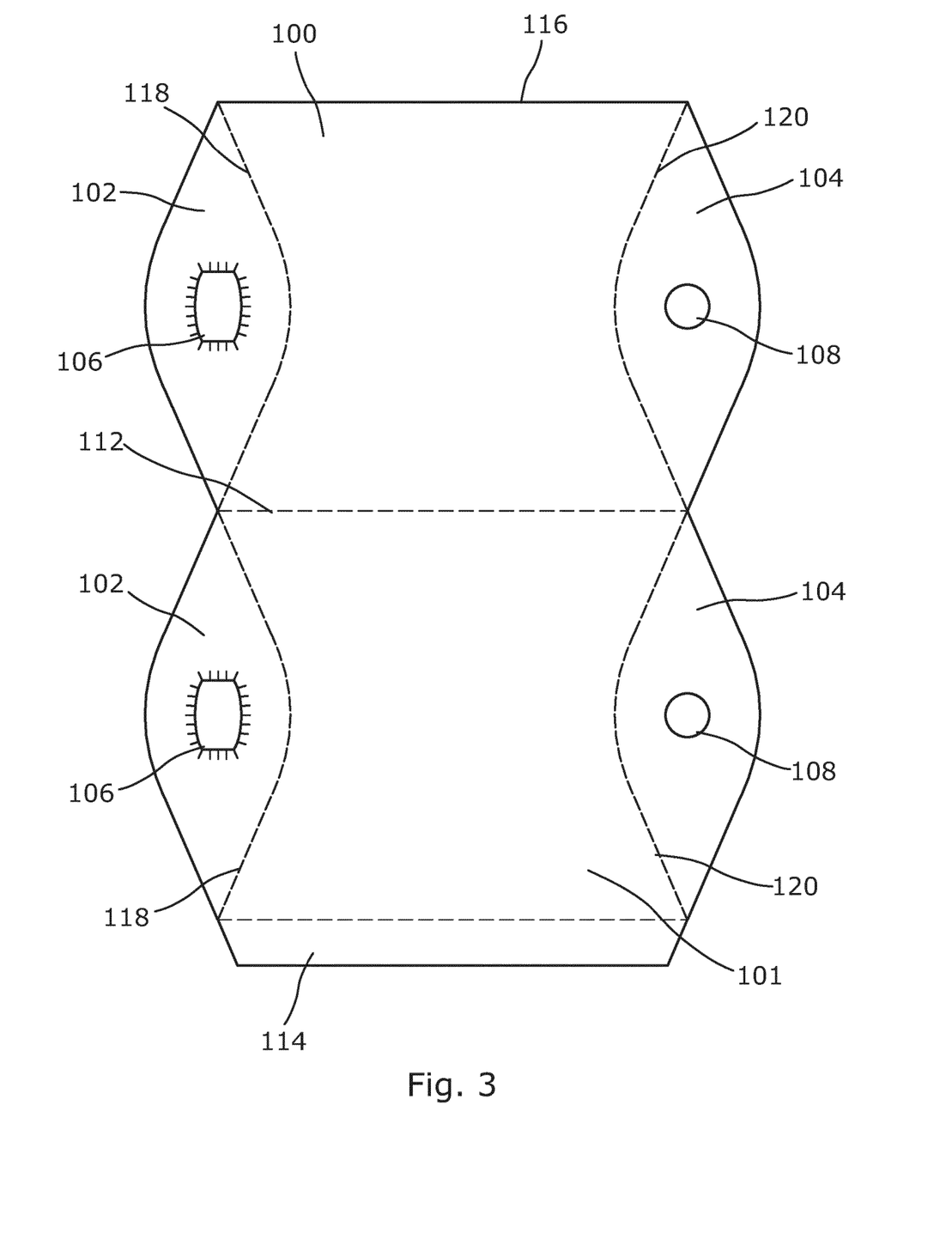
FIG. 3 shows an outline of a paperboard spacer blank used to manufacture a spacer of the present invention.

To form the spacer, the paperboard is first formed into a plurality of paperboard spacer blanks. FIG. 3 shows a plan view of the outline of a single paperboard spacer blank. The outline of the blank is shown in solid lines.

TABLE 2

Tensile strength and tearing resistance of SBB paperboard

| Grammage (g/m²) | 180 | 200 | 220 | 240 | 260 | 280 | 300 | 330 | 350 | 380 |
|---|---|---|---|---|---|---|---|---|---|---|
| Thickness (μm) | 205 | 235 | 260 | 300 | 330 | 360 | 395 | 435 | 465 | 505 |
| Bending stiffness (mNm) | | | | | | | | | | |
| Machine direction | 5.5 | 8.2 | 11.9 | 16.2 | 20.8 | 29.9 | 38.5 | 50.8 | 61.8 | 77.9 |
| Cross direction | 2.5 | 3.7 | 5.4 | 7.5 | 9.7 | 12.5 | 16 | 21 | 25 | 31 |
| Bending Resistance (mN) | | | | | | | | | | |
| Machine direction | 65 | 95 | 140 | 190 | 245 | 315 | 4.5 | 550 | 650 | 820 |
| Cross direction | 30 | 45 | 64 | 83 | 107 | 137 | 180 | 230 | 275 | 345 |
| Bending moment Taber (mNm) | | | | | | | | | | |
| Machine direction | 3.1 | 4.6 | 6.8 | 9.2 | 11.8 | 15.2 | 19.6 | 26.5 | 31.4 | 39.6 |
| Cross direction | 1.4 | 2.2 | 3.1 | 4 | 5.2 | 6.6 | 8.7 | 11.1 | 13.3 | 16.7 |
| Tensile strength (kN/m) | | | | | | | | | | |
| Machine direction | 17 | 18.5 | 20 | 21.5 | 23 | 24 | 25.5 | 28 | 29.5 | 31 |
| Cross direction | 9.5 | 10 | 10.5 | 11 | 11.5 | 12 | 12.5 | 13.5 | 14 | 14.5 |
| Tearing resistance (mN) | | | | | | | | | | |
| Machine direction | 2000 | 2300 | 2700 | 3100 | 3300 | 3700 | 4300 | 4700 | 5200 | 6400 |
| Cross direction | 2000 | 2350 | 2800 | 3300 | 3600 | 4000 | 4600 | 5100 | 5600 | 6400 |

Bending stiffness values are given in the table above. The inventor considers that bending stiffness is a particularly important property for achieving high foldability, folding endurance, and creasibility, of the paper spacer of the present invention.

The paperboard is stamped, or cut, along the solid lines to form the paperboard spacer blank. Preferably, where the spacer is to be mass-produced, multiple blanks may be stamped out from a single piece of paperboard, using one or more cutting die/stamp.

Once a paperboard spacer blank has been cut, creases are formed in it. Creases significantly increase the foldability of the paperboard by providing fold-lines, or hinges, about which the paperboard will preferentially fold when manipulated by a user. Creases 112, 118, 120 are illustrated with dotted lines in FIG. 3. The creases are formed in the paperboard of the spacer to form fold lines about which the spacer can be expanded and collapsed. When expanded, these creases form the edges of the spacer.

Without wishing to be bound by theory, it is thought that the bending moment of the paperboard is significantly reduced in the region of the crease, which encourages the paperboard to bend along the crease. In this way, the foldability is increased. A 'folding factor', which provides an indication of how easy a piece of paperboard is to fold after formation of a crease, is dependent on the bending moment.

$$\text{Folding factor} = ((M_{(uncreased)} - M_{(creased)})/M_{(uncreased)}) \times 100\%$$

where M is the bending factor.

The folding factor is effectively a measure of the change in bending moment (M) of a piece of paperboard before and after formation of a crease.

It is also considered that delamination of the laminar layers of fibres in the SBB paperboard help to increase foldability. By delaminating, the layers are able to move over each other more readily, thereby allowing the paperboard to bend.

The creases are formed by applying pressure to an upper portion of the paperboard spacer blank, thereby forming ridges/corrugations in the paperboard spacer blank. The creases do not include perforations.

Figure 4:
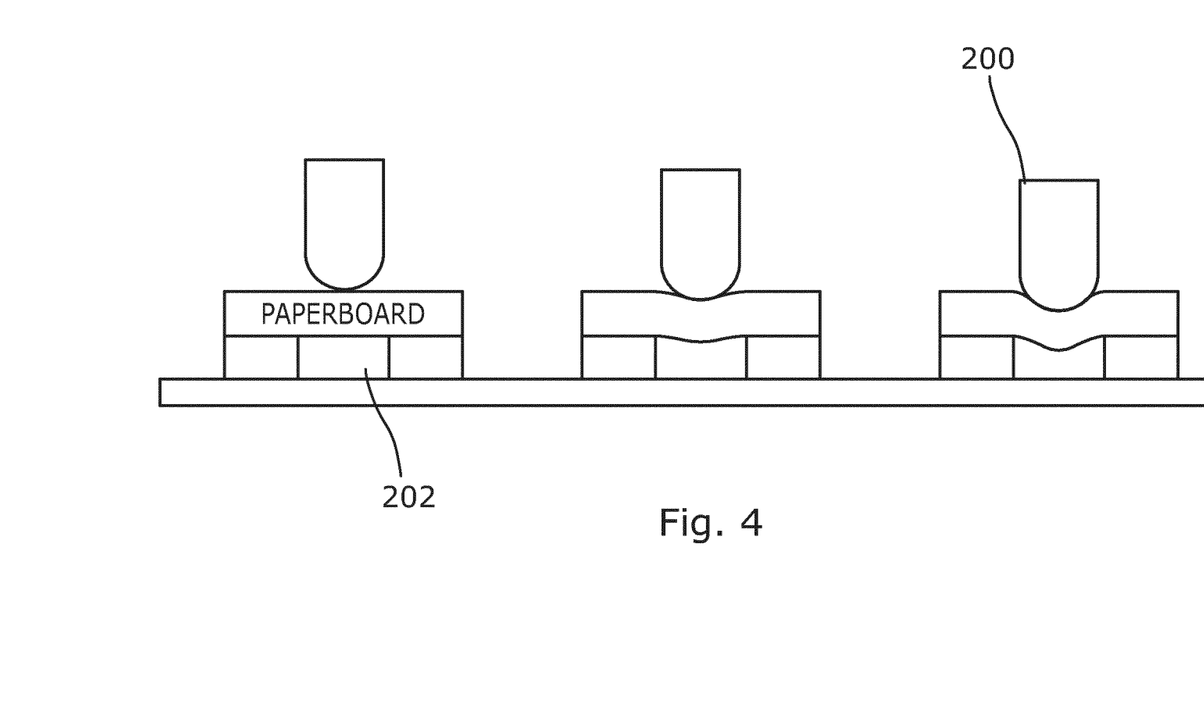
FIG. 4 shows a method of forming creases in a paperboard spacer blank.

The basic method used to form the creases in the paperboard spacer blank is shown in FIG. 4. Elongate creasing rule 200 is brought into contact with the paperboard, and pressure is applied to force the paperboard into a recess 202. A crease is thereby formed. For mass-producing the spacer product, the creasing rule 200 and recess 202 are provided in a die having a male part (carrying the creasing rule) and a female part (carrying the recess). When brought into contact, the creasing rule of the die engages the recess, to form the creases 112, 118, 120 as shown in FIG. 3.

By combining high foldability with an appropriate crease depth, excellent folding performance is achieved. Appropriate crease dimensions (width and depth) are given in Table 4.

TABLE 4

| Crease dimensions | | |
|---|---|---|
| Paperboard thickness (μm) | Crease width (mm) | Crease depth (mm) |
| 205 | 0.9 | 0.5 |
| 235 | 1.0 | 0.5 |
| 270 | 1.0 | 0.5 |
| 300 | 1.0 | 0.5 |
| 330 | 1.1 | 0.5 |
| 360 | 1.2 | 0.6 |
| 395 | 1.2 | 0.6 |
| 435 | 1.3 | 0.6 |
| 465 | 1.3 | 0.6 |
| 505 | 1.4 | 0.7 |

Once the paperboard spacer blank has been stamped/cut out, and the creases have been formed, the spacer can be assembled.

First, the paperboard spacer blank is folded along central crease 112. Tab 114 is then adhered to opposing edge 116 using glue, double-sided tape, or another suitable form of adhesion. This forms the collapsed configuration of the spacer.

The shape and properties of the spacer according to embodiments of the present invention will now be described.

Figure 5:
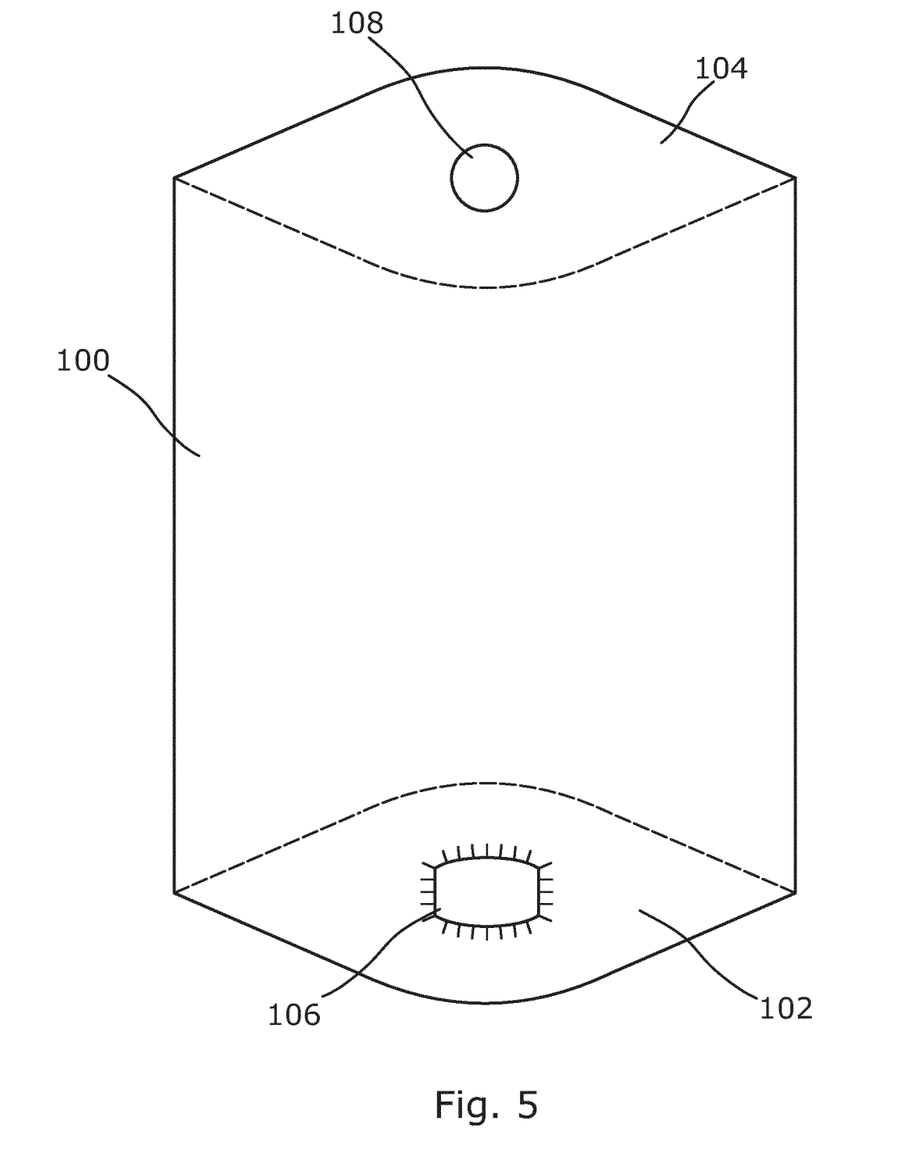
FIG. 5 shows a spacer of the present invention, in a collapsed configuration.

FIG. 5 shows the spacer in the collapsed configuration. When not in use (i.e. when packaged for sale, and being stored/transported by a user), the spacer is preferably kept in the collapsed configuration. Although not clear from FIG. 5, in the collapsed configuration the spacer has a substantially flat profile, with the upper and lower portions 100, 101, and first and second axial end portions 102, 104, all being substantially aligned with each other. Moreover, the upper and lower portions overlay one another, so that the spacer has effectively no internal cavity in the collapsed configuration. Accordingly, the total external volume occupied by the spacer is small in the collapsed configuration, and the spacer can be easily stored away.

To expand the spacer from the collapsed configuration to the expanded configuration, a user pushes the first and second axial end portions 102, 104 towards each other. This forces the first and second axial end portions 102, 104 to fold inwards. The first and second axial end portions are forced into a concave profile, which in turn forces the upper and lower portions into a convex profile, so that they form an internal cavity with an internal volume of 500 mL. This internal cavity provides an air flow-path between air inlet 106, and air outlet 108.

Figure 6A:
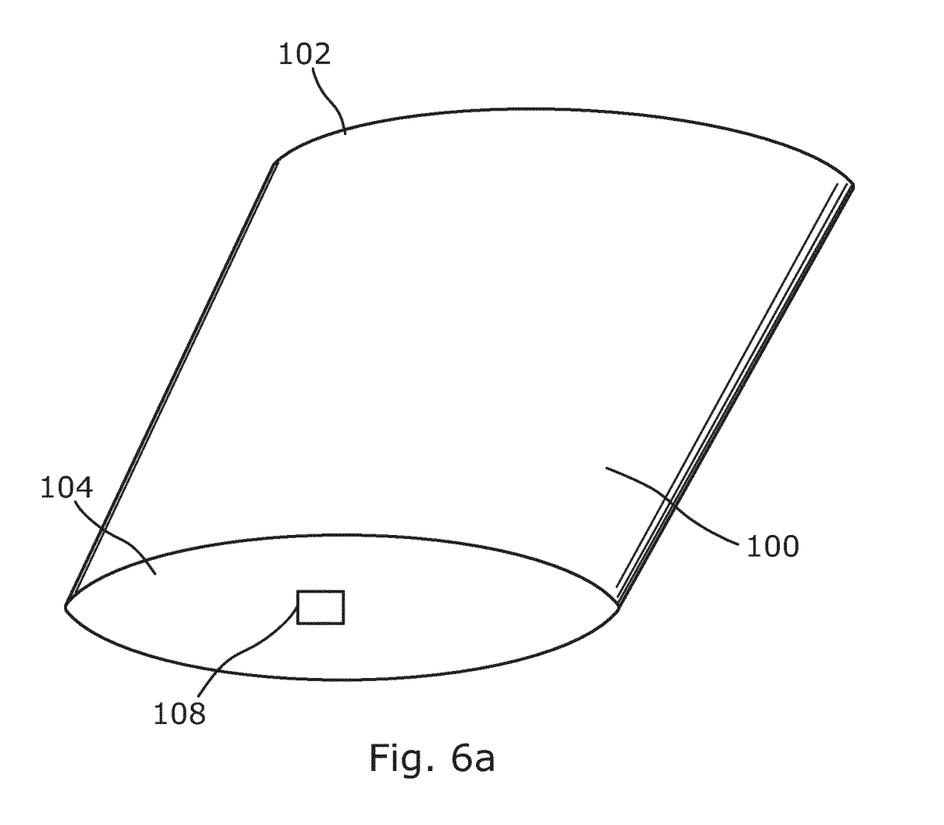
FIG. 6a shows a perspective view of the spacer of FIG. 5, in the expanded configuration.
Figure 6B:
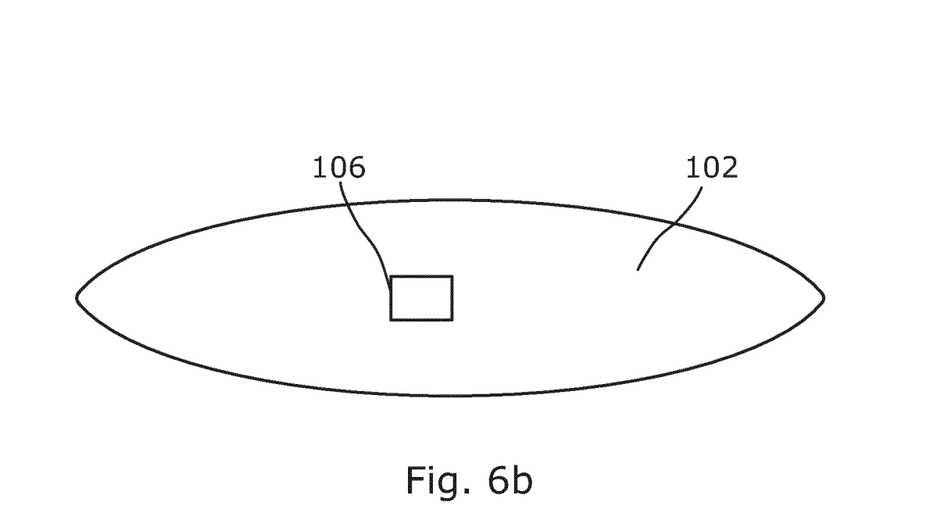
FIG. 6b shows an end-view of the spacer of FIGS. 5 and 6a, in the expanded configuration.

FIGS. 6a and 6b show respectively a perspective view, and an end-view, of a spacer formed by folding the paperboard spacer blank as above.

To collapse the spacer back into the collapsed configuration (i.e. from the expanded configuration), the user pushes the upper and lower portions towards each other. This forces the first and second axial end portions to fold away from each other, out of their concave profile. The volume of the air flow-path is reduced. Once the first and second axial end portions have folded outwards, and the upper and lower portions are in a planar, overlying arrangement, i.e. so that there is effectively no internal cavity, the spacer is back in the collapsed configuration.

Further features of the spacer will now be described, with references to FIGS. 6a and 6b. The same reference numerals are used for the common features of FIGS. 3 to 6b.

The spacer is shown in the expanded configuration, ready for use. Upper portion 100 and lower portion 101 are convex (in the expanded configuration shown), the convexity of the upper and lower portions defining a channel, or air flow-path with an internal volume of 500 mL. At a first end of the air flow-path is first axial end portion 102. At an opposing second end of the air flow path is second axial end portion 104. The first and second axial end portions are both concave (in the expanded configuration shown), and have a mandorla shape. The concavity of the first and second axial end portions maintains the convexity of the upper and lower portions in the expanded configuration. Inlet aperture 106 is formed in the first axial end portion 102. Inlet aperture 106 is an air inlet aperture through which air can enter the air flow path. Outlet aperture 108 is formed in the second axial end portion 104. Outlet aperture 108 is an air outlet aperture through which air can exit the air flow path. In the expanded configuration, the upper and lower portions have a generally perpendicular orientation relative to the first and second axial end portions.

As shown, axial end portions 102, 104 have the same shape and size. Moreover, axial end portions 102, 104 have a mandorla, e.g. bi-convex/lens shape.

Inlet aperture 106 has a shape and size selected to match that of the mouthpiece of an inhaler, e.g. pMDI inhaler. Inlet aperture 106 is configured to intimately engage the mouthpiece of an inhaler. There are less shape constraints on the outlet aperture 108, provided that it is of a size suitable for a user to inhale through it. Outlet aperture 108 may be square, rectangular, circular, or any other suitable shape.

Figure 7:
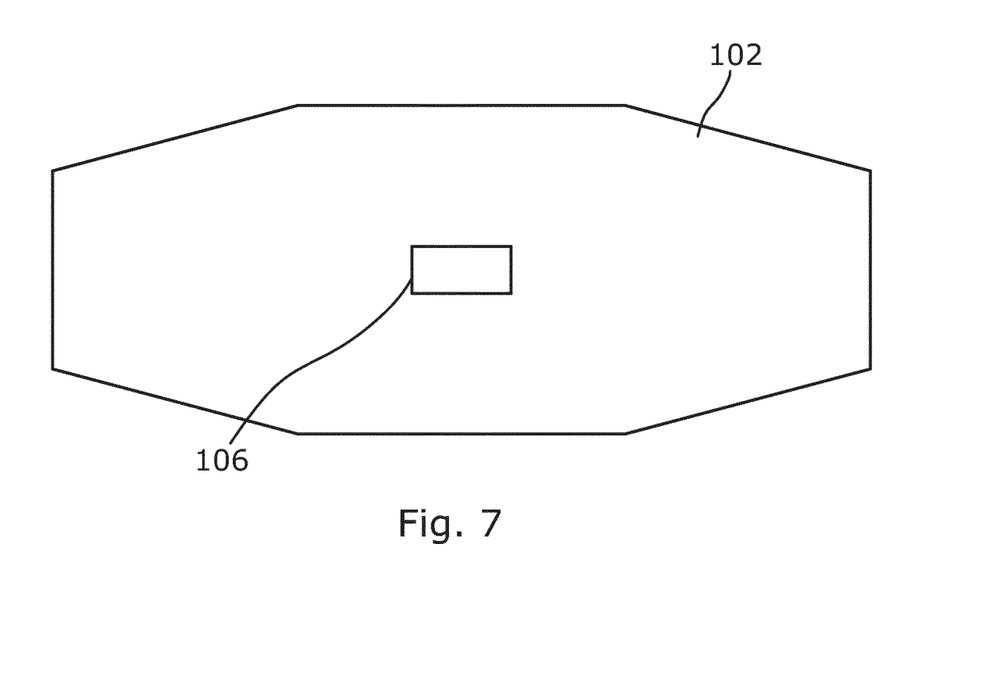
FIG. 7 shows an end-view of a spacer according to an embodiment of the present invention.
Figure 8:
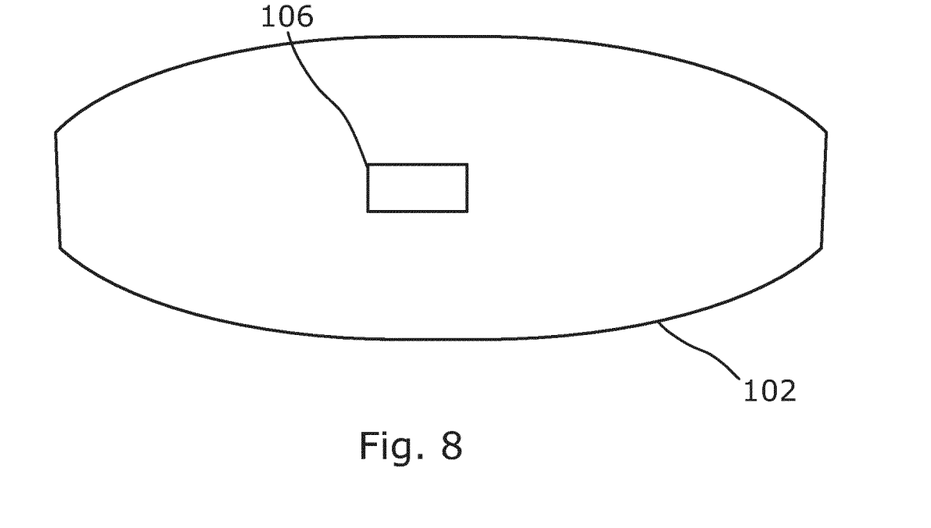
FIG. 8 shows an end-view of a spacer according to an embodiment of the present invention.

FIGS. 7 and 8 show end-views of spacers similar to the embodiment of FIGS. 6a and 6b. The spacers in FIGS. 7 and 8 have the same constituent parts as the spacer of FIGS. 6a and 6b. The only difference between the three embodiments is that the shape of the axial end portions 102, 104 is different in the embodiments of FIGS. 7 and 8. For brevity, only the end-views of the spacers in FIGS. 7 and 8 are shown. As shown, the axial end portions of the spacer in FIG. 7 have an octagonal shape. The end-sections of the spacer in FIG. 8 have a truncated lens shape.

The spacers of FIGS. 6a to 8 all have an internal cavity with a volume of 500 mL in the expanded configuration. In particular, the total volume of the air flow-path between the inlet aperture and the outlet aperture is 500 mL.

To use the spacer in the expanded configuration, a user secures inlet aperture 106 around the mouthpiece of a medical inhaler device. Through appropriate selection of the size and shape of the inlet aperture 106, the inhaler mouthpiece fits securely within the inlet aperture 106, secured by an interference fit. After securing the mouthpiece of the inhaler device in the inlet aperture, the user places his/her mouth over the outlet aperture 108. The user then activates the medical inhaler, e.g. by depressing a drug reservoir into the medical inhaler device in a manner that is well known in the art, in order to eject a dosage of aerosolized medication into the air flow path through the inlet aperture 106. A plume of low-velocity aerosolized medication forms in the air flow-path. After a short time (preferably within a few seconds), the user then inhales the plume into his/her lungs through the outlet aperture 108, preferably in a single deep breath.

The air flow path is 10 cm in length from the inlet aperture to the outlet aperture, and so provides a sufficient distance between the inlet aperture and outlet aperture for a low-velocity plume of aerosolized medication to form.

EXAMPLES

Figure 9:
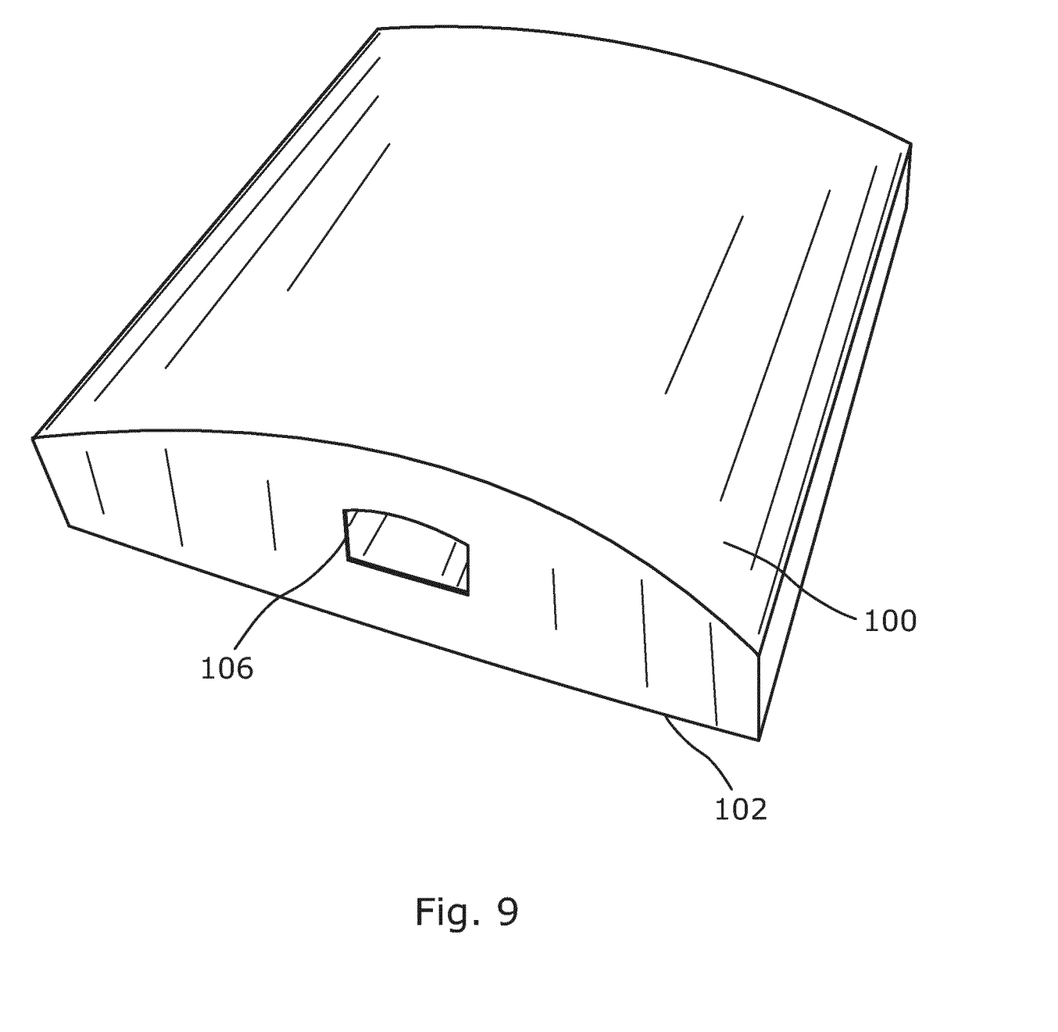
FIG. 9 shows a perspective view of the FIG. 8 spacer.

Testing of a spacer formed of InvercoteG™ 300 g/m$^2$ paperboard and having the shape as shown in FIGS. 8 and 9 was carried out by Intertek Laboratories (a certified oral inhaled product test laboratory) using a salbutamol MDI (Ventolin) inhaler.

In-vitro testing was conducted using the pharmacopoeia standard method, Next Generation Impactor (NGI).

The results are shown in the tables 5 and 6 below.

The results show oropharyngeal impaction decreases by 96%, from 48.2 µg (without a spacer) to 1.72 µg (with the paper spacer), and the dose delivered to the lungs increases by 53%, from 38.5% (without a spacer) to 91.3% (with the paper spacer).

TABLE 5

Ventolin (Salbutamol) MDI without spacer.

|  | Rep 1 | Rep 2 | Rep 3 | Rep 4 | Rep 5 | Rep 6 | Mean | % RSD |
|---|---|---|---|---|---|---|---|---|
| Actuator | 13.86279 | 15.41427 | 14.94708 | 16.90763 | 16.81952 | 18.31957 |  |  |
| T&M | 61.91560 | 60.50270 | 46.81165 | 41.60536 | 37.06972 | 41.06140 |  |  |
| Stg 1 | 1.11628 | 1.09677 | 1.34776 | 1.64124 | 1.84074 | 1.91750 |  |  |
| Stg 2 | 0.77108 | 0.82729 | 0.89789 | 1.09899 | 1.42038 | 1.25334 |  |  |
| Stg 3 | 2.03046 | 1.188765 | 2.47290 | 2.51813 | 3.07889 | 2.94964 |  |  |
| Stg 4 | 9.62803 | 8.91633 | 11.68725 | 12.66856 | 15.14915 | 13.73264 |  |  |
| Stg 5 | 13.55361 | 11.42877 | 13.11028 | 14.58565 | 14.14861 | 14.94634 |  |  |
| Stg 6 | 3.82522 | 3.25002 | 3.38248 | 3.89581 | 3.93912 | 3.78143 |  |  |
| Stg 7 | 1.11628 | 0.70937 | 0.63252 | 0.60781 | 1.02716 | 1.09150 |  |  |
| Stg 8 | 0.51429 | 0.48550 | 0.42300 | 0.36388 | 0.70669 | 0.67119 |  |  |
| Total | 107.829 | 104.519 | 95.713 | 95.893 | 95.198 | 99.725 |  |  |
| MMAD µm | 2.11226 | 2.15829 | 2.25585 | 2.24711 | 2.35996 | 2.27776 | 2.23521 | 3.94989 |
| GSD | 1.72014 | 1.73519 | 1.69033 | 1.70266 | 1.67122 | 1.72325 | 1.70713 | 1.38824 |
| FPD µg (≤5.0 µm) | 29.24229 | 25.81148 | 30.58593 | 33.47485 | 36.62443 | 35.80760 | 31.92443 | 12.98540 |
| FPF %* | 31.11989 | 28.96768 | 37.86993 | 42.38104 | 46.72767 | 43.98698 | 38.50887 | 18.67504 |

TABLE 6

Ventolin (Salbutamol) MDI with cardboard spacer

|  | Rep 1 | Rep 2 | Rep 3 | Rep 4 | Rep 5 | Rep 6 | Mean | % RSD |
|---|---|---|---|---|---|---|---|---|
| Actuator | 15.77754 | 14.64252 | 15.66382 | 15.38115 | 15.25622 | 12.75446 |  |  |
| Spacer | 13.68127 | 13.68832 | 8.37271 | 8.79331 | 9.47988 | 5.75052 |  |  |
| T&M | 1.17309 | 1.59985 | 1.16707 | 2.34275 | 1.51533 | 2.13277 |  |  |
| Stg 1 | 0.44807 | 0.56549 | 0.4032 | 0.44272 | 0.52036 | 0.34744 |  |  |
| Stg 2 | 0.64521 | 0.67345 | 0.55968 | 0.57529 | 0.71089 | 0.49322 |  |  |
| Stg 3 | 2.83231 | 2.50549 | 2.52936 | 2.58866 | 3.18891 | 2.20664 |  |  |
| Stg 4 | 18.75306 | 15.86145 | 15.90457 | 16.01341 | 18.80362 | 13.53822 |  |  |
| Stg 5 | 20.69419 | 17.60309 | 13.21422 | 16.15487 | 18.09864 | 15.54868 |  |  |
| Stg 6 | 4.92478 | 3.91624 | 4.04502 | 3.58644 | 3.83949 | 3.69073 |  |  |

TABLE 6-continued

Ventolin (Salbutamol) MDI with cardboard spacer

|  | Rep 1 | Rep 2 | Rep 3 | Rep 4 | Rep 5 | Rep 6 | Mean | % RSD |
|---|---|---|---|---|---|---|---|---|
| Stg 7 | 0.78636 | 0.65867 | 0.64139 | 0.61023 | 0.61441 | 0.61453 | | |
| Stg 8 | 0.48001 | 0.43094 | 0.453 | 0.42536 | 0.46348 | 0.42101 | | |
| Total | 80.196 | 72.147 | 63.954 | 66.914 | 72.491 | 573498 | | |
| MMAD μm | 2.19880 | 2.21576 | 2.35959 | 2.26444 | 2.30471 | 2.18145 | 2.25413 | 3.04801 |
| GSD | 1.52507 | 1.54536 | | 1.52316 | 1.52123 | 1.54377 | 1.52300 | 1.56455 |
| FPD μg (≤5.0 μm) | 47.35023 | 39.93963 | 36.78605 | 38.34816 | 43.74042 | 35.14805 | 40.21874 | 11.35788 |
| FPF %* | 93.32474 | 91.15354 | 92.15493 | 89.72485 | 91.59312 | 90.13860 | 91.34830 | 1.44848 |

NGI=Next Generation Impactor; T&M=Throat & Mouth Piece; MMAD=Mass Median Aerodynamic Diameter; GSD=Geometric Standard Deviation; FPD=Fine Particle Dose The FPD (Fine Particle Dose) in Tables 5 and 6 represents the respirable particles. The FTD values in the table 5 without spacer have a mean value of 31.9 μg whilst the FTD values in table 6 with cardboard spacer have a mean value of 40.2 μg. This corresponds to a 26% increase in respirable drug when the cardboard spacer is used.

The above embodiments have been described by way of example. Modifications of the above embodiments will be apparent to skilled persons on reading this disclosure and as such are within the scope of the invention.

The invention claimed is:

1. An inhalation spacer for use with a pressurised metered dose inhaler, the inhalation spacer being movable between a collapsed configuration for storage and transport, and an expanded configuration for use,
    wherein the spacer comprises upper and lower portions, and opposing axial end portions wherein an air inlet aperture and an air outlet aperture are formed therein,
    wherein, in the expanded configuration, the upper and lower portions define an air flow path between the air inlet aperture and the air outlet aperture and, in the collapsed configuration, the upper and lower portions are planar and overlay one another,
    wherein, to expand the spacer from the collapsed configuration to the expanded configuration, a user pushes the first and second axial end portions towards each other to force the first and second axial end portions to symmetrically fold inwards, and
    wherein the spacer is made from paperboard having a bending stiffness of at least 2.5 mNm.

2. The inhalation spacer according to claim 1 wherein the paperboard has a bending stiffness of between 3 mNm and 85 mNm.

3. The inhalation spacer according to claim 2 wherein the paperboard has a bending stiffness of between 5 mNm and 40 mNm.

4. The inhalation spacer according to claim 1 wherein the paperboard has a first bending stiffness in a machine direction and a second bending stiffness in a cross direction and wherein the first bending stiffness is between 35 and 40 mNm and/or the second bending stiffness is between 15 and 20 mNm.

5. The inhalation spacer according to claim 1 wherein the paperboard has a bending moment of at least 1 mNm.

6. The inhalation spacer according to claim 5 wherein the paperboard has a bending moment of between 1 mNm and 20 mNm.

7. The inhalation spacer according to claim 1 wherein the paperboard has a first bending moment in a machine direction and a second bending moment in a cross direction and wherein the first bending moment is between 17 and 22 mNm and/or the second bending moment is between 5 and 10 mNm.

8. The inhalation spacer according to claim 1 wherein the paperboard has a tensile strength of at least 9 kN/m.

9. The inhalation spacer according to claim 8 wherein the paperboard has a tensile strength of between 9 kN/m and 35 kN/m.

10. The inhalation spacer according to claim 1 wherein the paperboard has a first tensile strength in a machine direction and a second tensile strength in a cross direction and wherein the first tensile strength is between 20 kN/m and 30 kN/m and/or the second tensile strength is between 10 kN/m and 15 kN/m.

11. The inhalation spacer according to claim 1 wherein the paperboard has a tearing resistance of at least 1800 mN.

12. The inhalation spacer according to claim 11 wherein the paperboard has a tearing resistance of between 3500 and 6500 mN.

13. The inhalation spacer according to claim 1 wherein the paperboard has a first tearing resistance in a machine direction and a second tearing resistance in a cross direction and wherein the first tearing resistance is around 4300 mN and/or the second tearing resistance is around 4600 mN.

14. The inhalation spacer according to claim 1 wherein the paperboard has an area density of between 180 and 995 g/m$^2$.

15. The inhalation spacer according to claim 14 wherein the paperboard has an area density of between 250 and 400 g/m$^2$.

16. The inhalation spacer according to claim 1 wherein the paperboard comprises fibres having a length between 0.9 and 1.2 mm and/or fibres having a length between 2 and 3 mm and/or fibres having a length between 3.1 and 3.5 mm.

17. The inhalation spacer according to claim 16 wherein the paperboard comprises fibres having a length between 0.9 and 1.2 mm derived from a first wood source and/or fibres having a length between 2 and 3 mm derived from a second wood source and/or fibres having a length between 3.1 and 3.5 mm derived from a third wood source.

18. The inhalation spacer according to claim 1 wherein the paperboard is virgin paperboard.

19. The inhalation spacer according to claim 1 wherein the paperboard is a solid bleached paperboard.

20. The inhalation spacer according to claim 1 wherein, in the expanded configuration, the spacer has internal cavity, the internal cavity providing an air flow-path between an inlet aperture and an outlet aperture, the internal cavity having a volume of 500 mL or more.

* * * * *